US00PP37435P2

(12) United States Plant Patent
Koot

(10) Patent No.: US PP37,435 P2
(45) Date of Patent: May 19, 2026

(54) ***CALIBRACHOA* PLANT NAMED 'Docalraidraber'**

(50) Latin Name: *Calibrachoa parviflora*
Varietal Denomination: Docalraidraber

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 19/344,632

(22) Filed: Sep. 30, 2025

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Calibrachoa* plant named 'Docalraidraber', characterized by its upright to outwardly spreading and mounding plant habit with plants eventually becoming trailing and decumbent; vigorous growth habit and moderate growth rate; freely branching habit; early and freely flowering habit; large flowers with purplish pink and deep red bi-colored petals yellowish-colored centers; and good container and garden performance.

1 Drawing Sheet

Botanical designation: *Calibrachoa parviflora.*
Cultivar denomination: 'DOCALRAIDRABER'.

BACKGROUND OF THE INVENTION

The present invention relates to a new and distinct cultivar of *Calibrachoa* plant, botanically known as *Calibrachoa parviflora* and hereinafter referred to by the name 'Docalraidraber'.

The new *Calibrachoa* plant is a product of a planned breeding program conducted by the Inventor in Rheinberg, Germany. The objective of the breeding program is to create new freely branching and early-flowering *Calibrachoa* plants with numerous large flowers with an interesting color pattern.

The new *Calibrachoa* plant originated from a cross-pollination made by the Inventor in July 2022 in Rheinberg, Germany of a proprietary selection of *Calibrachoa parviflora* identified as code number AA22-K0152, not patented, as the female, or seed, parent with a proprietary selection of *Calibrachoa parviflora* identified as code number AA22-K0249, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in April 2023.

Asexual reproduction of the new *Calibrachoa* plant by vegetative terminal cuttings in a controlled greenhouse environment in Rheinberg, Germany since April 2023 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docalraidraber'. These characteristics in combination distinguish 'Docalraidraber' as a new and distinct *Calibrachoa* plant:

1. Upright to outwardly spreading and mounding plant habit with plants eventually becoming trailing and decumbent.
2. Vigorous growth habit and moderate growth rate.
3. Freely branching habit.
4. Early and freely flowering habit.
5. Large flowers with purplish pink and deep red bi-colored petals yellowish-colored centers.
6. Good container and garden performance.

The new *Calibrachoa* can be compared to plants of the female parent selection. Plants of the new *Calibrachoa* differ primarily from plants of the female parent selection in the following characteristics:

1. Plants of the new *Calibrachoa* are more vigorous than and not as compact as plants of the female parent selection.
2. Plants of the new *Calibrachoa* are more freely branching than plants of the female parent selection.
3. Plants of the new *Calibrachoa* are denser than and not as open as plants of the female parent selection.
4. Plants of the new *Calibrachoa* have larger and more rounded flowers than plants of the female parent selection.
5. Flowers of plants of the new *Calibrachoa* are purplish pink and deep red bi-colored petals yellowish-colored centers whereas flowers of plants of the female parent selection are light pink in color with darker pink-colored centers.

The new *Calibrachoa* can be compared to plants of the male parent selection. Plants of the new *Calibrachoa* differ primarily from plants of the male parent selection in the following characteristics:

1. Plants of the new *Calibrachoa* are more mounding and denser than and not as open as plants of the male parent selection.
2. Plants of the new *Calibrachoa* are more freely branching than plants of the male parent selection.
3. Plants of the new *Calibrachoa* have more rounded and flatter flowers than plants of the male parent selection.
4. Flowers of plants of the new *Calibrachoa* are purplish pink and deep red bi-colored petals yellowish-colored centers whereas flowers of plants of the male parent selection are pink in color with yellow-colored centers.

Plants of the new *Calibrachoa* can also be compared to plants of *Calibrachoa* sp. 'Ombre Pink', not patented. In side-by-side comparisons, plants of the new *Calibrachoa* differ primarily from plants of 'Ombre Pink' in the following characteristics:

1. Plants of the new *Calibrachoa* are larger than plants of 'Ombre Pink'.
2. Plants of the new *Calibrachoa* are more freely branching than plants of 'Ombre Pink'.
3. Plants of the new *Calibrachoa* are more freely flowering than plants of 'Ombre Pink'.
4. Plants of the new *Calibrachoa* have more rounded and flatter flowers than plants of 'Ombre Pink'.
5. Flowers of plants of the new *Calibrachoa* are purplish pink and deep red bi-colored petals yellowish-colored centers whereas flowers of plants of 'Ombre Pink' are soft pink in color with reddish-colored centers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant. The photograph is a side perspective view of a typical flowering plant of 'Docalraidraber' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Plants were twelve weeks old when the photograph was taken and 25 weeks old when the detailed description was taken. In the following description, color references are made to The Royal Horticultural Society Colour Chart, Fifth Edition, except where general terms of ordinary dictionary significance are used.

Botanical classification: *Calibrachoa parviflora* 'Docalraidraber'.

Parentage:

*Female, or seed, parent*.—Proprietary selection of *Calibrachoa parviflora* identified as code number AA22-K0152, not patented.

*Male, or pollen, parent*.—Proprietary selection of *Calibrachoa parviflora* identified as code number AA22-K0249, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and mounding plant habit with plants eventually becoming trailing and decumbent; vigorous growth habit and moderate growth rate; freely branching habit with about eleven primary lateral branches each with about ten secondary lateral branches developing per plant; pinching enhances branching potential; dense and full appearance.

*Plant height, soil level to top of foliar plane*.—About 23 cm.

*Plant height, soil level to top of floral plane*.—About 23 cm.

*Plant diameter* (*spread of plant*).—About 64 cm.

Lateral branch description:

*Length*.—About 43.6 cm.

*Diameter*.—About 4 mm.

*Internode length*.—About 2.8 mm.

*Strength*.—Strong.

*Aspect*.—Initially upright to outwardly spreading and eventually trailing and decumbent.

*Texture and luster*.—Pubescent; glossy.

*Color, developing*.—Close to 144A.

*Color, developed*.—Close to 146C; at the internodes, close to 144A.

Leaf description:

*Arrangement*.—Before flowering, alternate, and after flowering, opposite; simple.

*Length*.—About 3 cm.

*Width*.—About 1 cm.

*Shape*.—Oblanceolate.

*Apex*.—Rounded.

*Base*.—Attenuate.

*Margin*.—Entire.

*Texture and luster, upper and lower surfaces*.—Pubescent; matte.

*Venation pattern*.—Pinnate; arcuate.

*Color*.—Developing leaves, upper surface: Close to 137B. Developing leaves, lower surface: Close to 138A. Fully expanded leaves, upper surface: Close to 137A; venation, close to 147C. Fully expanded leaves, lower surface: Close to 147B; venation, close to 147C.

*Petioles*.—Length: About 5.6 mm. Diameter: About 5 mm. Strength: Moderately strong. Texture and luster, upper and lower surfaces: Pubescent; matte. Color, upper and lower surfaces: Close to 147C.

Flower description:

*Flower arrangement and habit*.—Single rounded and salverform flowers arising from leaf axils; freely flowering habit with usually about 924 flowers and flower buds developing per plant during the flowering season; flowers face mostly upright to somewhat outwardly.

*Fragrance*.—None detected.

*Natural flowering season*.—Early flowering habit, plants of the new *Calibrachoa* begin flowering about four weeks after planting rooted young plants; plants flower continuously from the spring throughout the summer in Germany.

*Flower longevity*.—Individual flowers last about seven to ten days on the plant; flowers not persistent.

*Flower buds*.—Length: About 2.4 cm. Diameter: About 5 mm. Shape: Elongated oblong. Texture and luster: Rippled; semi-glossy. Color: Close to 150B and 150D.

*Flower diameter*.—About 3.2 cm by 3.5 cm.

*Flower depth* (*height*).—About 3 cm.

*Flower throat diameter*.—About 6.4 mm.

*Flower tube length*.—About 1.9 cm.

*Flower tube diameter, distally*.—About 6.5 mm.

*Corolla*.—Arrangement: Five petals fused at the base and opening into a flared trumpet. Petal length from throat: About 1.4 cm. Petal lobe width: About 1.7 cm. Petal shape: Roughly spatulate. Petal apex: Rounded. Petal margin: Entire; slightly undulate. Petal texture and luster, upper and lower surfaces: Smooth, glabrous; matte. Throat texture: Smooth, glabrous. Tube texture: Smooth, glabrous. Color: Petal, when opening, upper surface: Distally, close to 59A and proximally, close to 4A and 4C. Petal, when opening, lower surface: Close to 4C, 10C, 64A and 75C. Petal, fully opened, upper surface: Distally, close to 65A and 65B; towards the base, close to 60A; at the base, close to 20A; venation, close to 164C; main color becoming closer to 65B with subsequent development. Petal, fully opened, lower surface: Close to 11A, 65B and 65D; venation, close to N144B; color becoming closer to 65D with subsequent development. Throat: Close to 7A and 60A; venation, close to 177C. Tube: Close to 151C; venation, close to N144B.

*Calyx*.—Arrangement: Star-shaped calyx with five sepals; sepals fused at the base. Sepal length: About 8.4 mm. Sepal width: About 3 mm. Sepal shape: Lanceolate. Sepal apex: Acute. Sepal margin: Entire. Sepal texture and luster, upper and lower surfaces: Pubescent; matte. Color: When developing and fully opened, upper surface: Close to 146A and 146D. When developing and fully opened, lower surface: Close to 146A and 146D.

*Peduncles*.—Length: About 1.7 cm. Diameter: About 1 mm. Angle: About 45° from lateral branch axis. Strength: Moderately strong. Texture and luster: Pubescent; matte. Color: Close to 144B.

*Reproductive organs*.—Stamens: Quantity: Five per flower. Filament length: About 5 mm. Filament color: Close to 145C. Anther length: About 1 mm. Anther shape: Ellipsoidal. Anther color: Close to 16B. Pollen amount: Scarce. Pollen color: Close to 16B. Pistils: Quantity: One per flower. Pistil length: About 9 mm. Style length: About 8 mm. Style color: Close to 144B Stigma diameter: About 1 mm. Stigma shape: Ellipsoidal. Stigma color: Close to 144A. Ovary color: Close to 144C. Fruits: Quantity produced per plant: About 320 develop per plant during the flowering season. Length: About 1 cm. Diameter: About 3 mm. Texture: Smooth, glabrous. Color: Close to 164A. Seeds: Quantity per flower: About 25. Length: About 1 mm. Diameter: About 1 mm. Texture: Smooth, glabrous. Color: Close to 200B.

Garden performance: Plants of the new *Calibrachoa* have been observed to have good garden performance and to tolerate wind, rain, temperatures ranging from about 5° C. to about 40° C. and to be suitable for USDA Hardiness Zone 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Docalraidraber' as herein illustrated and described.

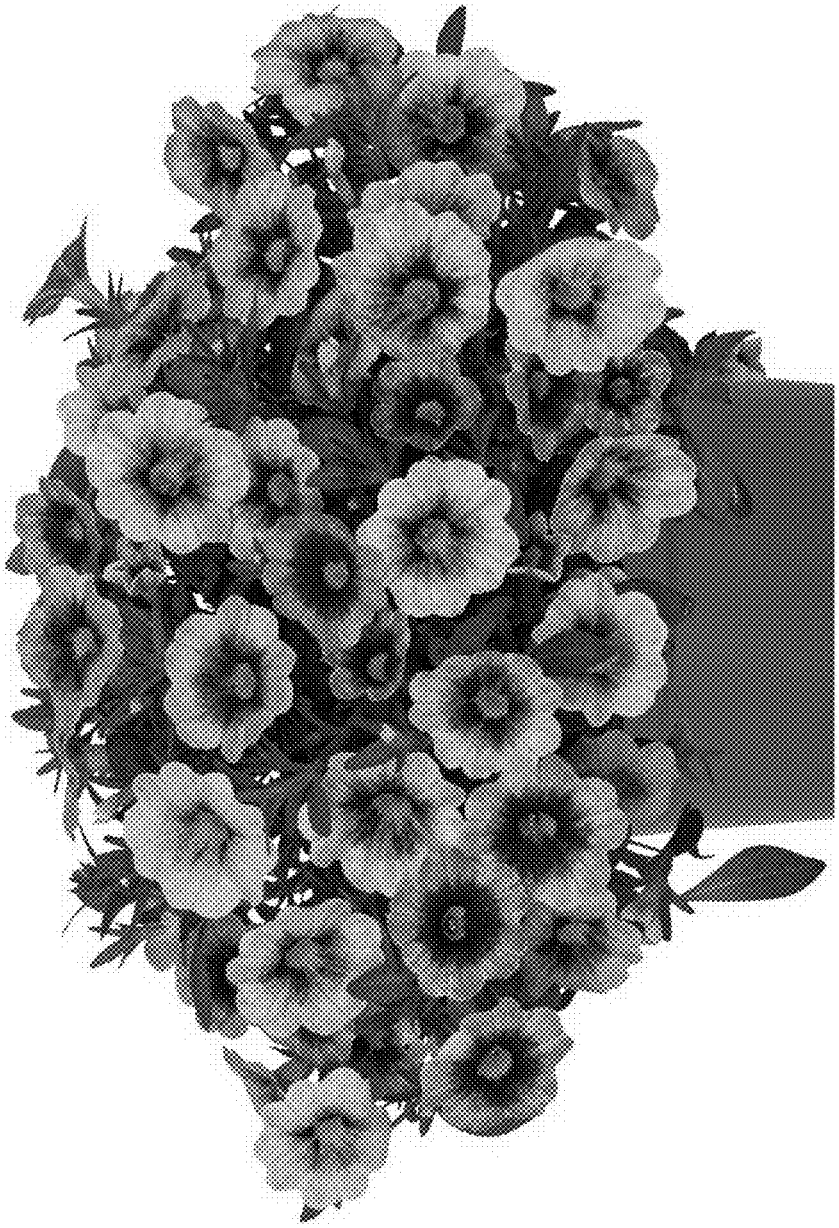

* * * * *